United States Patent
Kashiwagi et al.

(10) Patent No.: US 9,221,753 B2
(45) Date of Patent: Dec. 29, 2015

(54) PROCESS FOR THE SYNTHESIS OF VITAMIN D COMPOUNDS AND INTERMEDIATES FOR THE SYNTHESIS OF THE COMPOUNDS

(75) Inventors: Hirotaka Kashiwagi, Gotenba (JP); Yoshiyuki Ono, Gotenba (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 1965 days.

(21) Appl. No.: 10/588,201

(22) PCT Filed: Feb. 3, 2005

(86) PCT No.: PCT/JP2005/001586
§ 371 (c)(1),
(2), (4) Date: Aug. 2, 2006

(87) PCT Pub. No.: WO2005/074389
PCT Pub. Date: Aug. 18, 2005

(65) Prior Publication Data
US 2007/0135394 A1     Jun. 14, 2007

(30) Foreign Application Priority Data
Feb. 3, 2004 (JP) .................................. 2004-26291

(51) Int. Cl.
A61K 31/59     (2006.01)
C07C 401/00    (2006.01)
C07F 7/18      (2006.01)

(52) U.S. Cl.
CPC ............. *C07C 401/00* (2013.01); *C07F 7/1892* (2013.01)

(58) Field of Classification Search
USPC .......................................... 553/653; 514/167
See application file for complete search history.

(56) References Cited

U.S. PATENT DOCUMENTS

| | | | |
|---|---|---|---|
| 5,827,883 A | 10/1998 | Barbier et al. | |
| 6,030,962 A | 2/2000 | Manchand et al. | |
| 6,080,878 A | 6/2000 | De Los Angeles Rey et al. | |

FOREIGN PATENT DOCUMENTS

| | | |
|---|---|---|
| JP | 10 502940 | 3/1998 |
| JP | 10 316652 | 12/1998 |
| JP | 2000-510875 | 8/2000 |

OTHER PUBLICATIONS

Gul-Dong Zhu et al. (Chem. Rev. 1995, 95, 1877-1852).*
Basil Lythgoe et al. (J.C.S. Perkin I, 2386-2390, published Jan. 1, 1976).*
Dorwald F. A. Side Reactions in Organic Synthesis, 2005, Wiley: VCH, Weinheim p. IX of Preface.*
Lars K. A. Blaehr et al., Steroids, Steroids 66 (2001), pp. 539-548, "Polyclonal antibodies to EB1089 (seocalcitol), an analog of 1a,25-dihydroxyvitamin $D_3$".
Enrico G. Baggiolini et al., J. American Chemical Society, 104 (1982), pp. 2945-2948, "Stereoselective Total Synthesis of 1a,25-Dihydroxycholecalciferol".
Enrico G. Baggiolini et al., J. Org. Chemical, 51 (1986), pp. 3098-3108. "Stereoselective Total Synthesis of 1a,25-Dihydroxycholecalciferol".
Gui-Dong Zhu et al., Chemical. Rev., 95 (1995), pp. 1877-1952, "Synthesis of Vitamin D (Calciferol)".
Anthony W. Norman et al., J. Med. Chem., 43 (2000), pp. 2719-2730, "Characterization of a Novel Analogue of 1a,25$(OH)_2$-Vitamin $D_3$ with Two Side Chains: Interaction with Its Nuclear Receptor and Cellular Actions".
Shian-Jan Shiuey et al., J. Org. Chem., 55 (1990), pp. 243-247, "Total Synthesis of 1a-Fluro-25-hydroxycholecalciferol and -ergocalciferol".
Rafal R. Sicinski et al., J. Med. Chem., 41 (1998), pp. 4662-4674, "New 1a,25-Dihydroxy-19-norvitamin $D_3$ Compounds of High Biological Activity: Synthesis and Biological Evaluation of 2-Hydroxymethyl, 2-Methyl, and 2-Methylene Analogues".
Yusheng Wu et al., Bioorganic & Medicinal Chemistry Letters, 12 (2002), pp. 1633-1636, "Vitamin $D_3$:Synthesis of seco-C-9,11-bisnor-17-Methyl-1a, 25-dihydroxyvitamin $D_3$ Analogues".
A. Kutner et al., Bioorganic & Medicinal Chemistry, 23 (1995), pp. 22-32, "Synthesis of Retiferol $RAD_1$ and $RAD_2$, the Lead Representatives of a New Class of des-CD Analogs of Cholecalciferol".
Paul E. Peterson et al., J. Org. Chem, 51 (1986), pp. 1948-1954, "Studies of the Ketone Obtained from the Ozonolysis of Vitamin D. Molecular Mechanics Calculations for it and Related Hydrindanones$^{1a}$".
Gary H. Posner et al., J. Med. Chem., 35 (1992), pp. 3280-3287, "New Vitamin $D_3$ Derivatives with Unexpected Antiproliferative Activity: 1-(Hydroxymethyl)-25-hydroxyvitamin $D_3$ Homologs".
Susumi Hatakeyama et al., Bioorganic & Medicinal Chemistry, 9 (2001), pp. 403-415, "Synthesis and Evaluation of A-Ring Diastereomers of 1a,25-Dihydroxy-22-Oxavitamin $D_3$ $(OCT)^1$ ".
Baggiolini et al., Stereocontrolled Total Synthesis of 1α,25-Dihydroxycholecalciferol1 and 1α,25-Dihydroxyergocalciferol, J. Org. Chem., 51:3098-3108 (1986).

* cited by examiner

*Primary Examiner* — Sabiha N Qazi
(74) *Attorney, Agent, or Firm* — Browdy and Neimark, PLLC

(57) ABSTRACT

An object of the present invention is to provide a process for synthesizing a vitamin D compound by simple procedures at lower costs.

The present invention provides a process for preparing a vitamin D compound and an intermediate thereof, comprising the step of: (a) mixing a ketone or aldehyde, a Wittig reagent, and a base; or (b) mixing a ketone or aldehyde and a Wittig reagent, and then adding a base to the resulting mixture.

6 Claims, No Drawings

PROCESS FOR THE SYNTHESIS OF VITAMIN D COMPOUNDS AND INTERMEDIATES FOR THE SYNTHESIS OF THE COMPOUNDS

TECHNICAL FIELD

The present invention relates to novel processes for synthesizing vitamin D compounds useful as medicines and their intermediates.

BACKGROUND ART

Vitamin D compounds are known to show a wide variety of physiological activities such as calcium metabolism regulation, growth inhibition or differentiation induction of tumor cells or the like, immunoregulation, etc.

Vitamin D compounds and their intermediates are commonly synthesized by using methods based on the Wittig-Horner reaction.

The Wittig-Horner reaction generally refers to a series of reactions where a Wittig reagent obtained from an alkyl halide and a triphenyl phosphate ester is reacted with a strong base to form a phosphonium ylide, the ylide adds to an aldehyde or ketone to form an adduct and, then, a phosphine oxide is removed from the adduct (oxaphosphetane) to give an olefin.

The Wittig-Horner reaction is performed by adding a base dropwise to a Wittig reagent to produce a ylide and then adding a ketone or aldehyde to the ylide, or by mixing a Wittig reagent and a ketone or aldehyde and then adding a base dropwise to the resulting mixture (Blahr L. et al., Steroides, 66, 2001, 539) or other methods, among which only the first method is used for the synthesis of vitamin D compounds. This is because the second method or other methods cannot be expected to provide a sufficient yield due to the epimerization of a ketone used as a starting material or the nucleophilic reaction of the anion of a base added (e.g., n-butyl anion is formed when n-butyl lithium is added as a base) to the carbonyl group on the ketone or aldehyde, whereby the ketone or aldehyde is consumed.

Specifically, the synthesis of a vitamin D compound begins by adding a strong base such as n-butyl lithium, phenyl lithium, methyl lithium or lithium diisopropylamide dropwise to a Wittig reagent which is an A-ring intermediate of the vitamin D in tetrahydrofuran at an extremely low temperature, normally −78° C., to produce a ylide. Then, a solution of a ketone which is a CD-ring intermediate of the vitamin D in tetrahydrofuran is added to the ylide at an extremely low temperature, normally −78° C. Then, the mixed solution is stirred between −78° C. and room temperature to form a trans-diene structure characteristic of vitamin D. This method is widely used for synthesizing various vitamin D compounds and their intermediates because a relatively good yield and high stereoselectivity can be obtained (Baggiolini E. et al., J. Am. Chem. Soc., 104, 1982, 2945, Baggiolini E. et al., J. Org. Chem., 51, 1986, 3098, Zhu G. et al., Chem. Rev., 95, 1995, 1877, Norman A. et al., J. Med. Chem., 43, 14, 2000, 2719, Shiuey S. et al., J. Org. Chem., 55, 1990, 243, Sicinski, R. et al., J. Med. Chem., 41, 23, 1998, 4662, Wu Y. et al., Bioorg. Med. Chem. Lett., 12, 12, 2002, 1633, Kutner A. et al., Bioorg. Chem., 23, 1, 1995, 22). This method is also used for synthesizing vitamin D compounds and their intermediates using an aldehyde instead of a ketone as a CD-ring intermediate (Wu Y. et al., Bioorg. Med. Chem. Lett., 12, 12, 2002, 1633).

A typical example of a synthetic scheme of vitamin D compounds via the Wittig-Horner reaction is shown below.

Conventional Synthetic Method

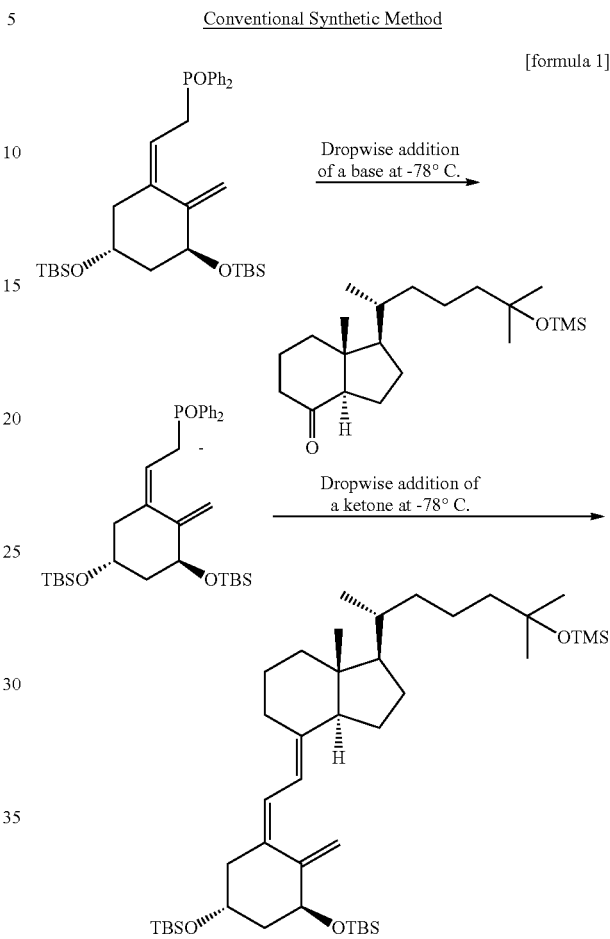

[formula 1]

It is known that several side reactions occur during the Wittig-Horner reaction. One of them is induced by moisture inclusion so that the ylide is lost. Another side reaction is epimerization of the ketone which is caused by rise of the reaction temperature (Baggiolini E. et al., J. Am. Chem. Soc., 104, 1982, 2945, Baggiolini E. et al., J. Org. Chem., 51, 1986, 3098, Peterson P. et al., J. Org. Chem., 51, 1986, 1948). Still another side reaction is nucleophilic addition to the carbonyl group on the ketone or aldehyde. If these side reactions occur, the yield of vitamin D compounds decreases.

Two side reactions accompanying the Wittig-Horner reaction are shown below.

Side reaction induced by moisture inclusion

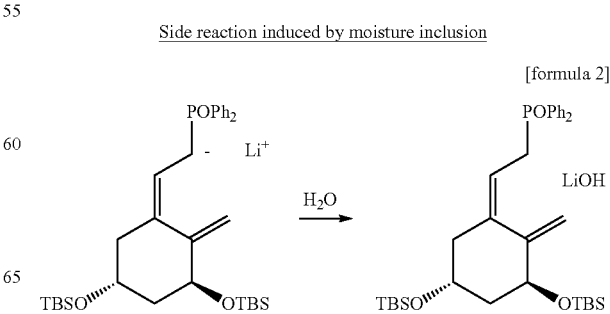

[formula 2]

3
-continued
Side reaction induced by temperature rise (epimerization)

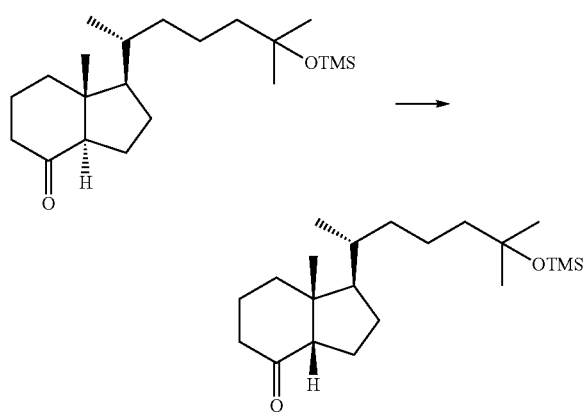

In order to avoid these side reactions to afford intended vitamin D compounds with high yield, in conventional methods for vitamin D synthesis, it was necessary to prevent moisture inclusion into the reaction system and to perform mixing procedures under low temperature conditions. In addition to the step of adding a solution of a ketone in tetrahydrofuran to the produced ylide, which must be performed at low temperature, normally −78° C., to prevent epimerization, the preceding step of adding a base such as n-butyl lithium dropwise to a Wittig reagent has also been conventionally performed at a low temperature, normally −78° C. Under such low temperature conditions, moisture inclusion due to condensation or the like and temperature rise which may induce side reactions would be more likely to occur. Hence, very complex mixing procedures have been required to prevent the side reactions.

In an industrial large-scale synthesis of vitamin D compounds, tremendous amounts of cost for facility, labor, energy or the like and time have been required to prevent moisture inclusion and to maintain an extremely low temperature environment. On the other hand, in a so-called laboratory scale synthesis of vitamin D compounds where a small amount of compound on the order of 10 to 20 mg is synthesized, the yield was very low or no intended product could be obtained (Posner G. et al., J. Med. Chem., 35, 1992, 3280). This is because it is difficult to prevent moisture inclusion and maintain an extremely low temperature environment even by using a syringe or cannula or the like and the above side reactions are more likely to occur especially due to complex mixing procedures during the small-scale synthesis on the order of 10 to 20 mg.

It is believed that intended vitamin D compounds could be theoretically obtained in good yield by using equivalent amounts of a Wittig reagent and a ketone or aldehyde. However, conventional methods have failed to sufficiently prevent side reactions and have required much cost and time to sufficiently prevent them as described above, and therefore, an excess of about 0.5 equivalents to 1 equivalent of either a Wittig reagent or a ketone or aldehyde has been typically used to prevent the yield loss resulting from side reactions, which has further added production costs.

Unreacted Wittig reagent and ketone or aldehyde can be recovered by a silica gel column or the like to avoid the waste of starting materials (Baggiolini E. et al., J. Org. Chem., 51, 1986, 3098, Hatakeyama S. et al., Bioorg. Med. Chem. 9, 2001, 403), but recovery procedures require cost and time and epimerized ketones are often unrecoverable.

4
DISCLOSURE OF THE INVENTION

Problems to be Solved by the Invention

As described above, conventional methods for synthesizing vitamin D compounds require very complex procedures to obtain sufficient yield and also require high cost and long period for industrial scale production. In laboratory scale production in small amounts, only very low yield could be expected. Therefore, there is a need for a method for synthesizing vitamin D compounds by simple procedures at low costs.

Means for Solving the Problems

The present invention solves the problems of the conventional techniques described above.

Accordingly, the present invention provides a process for preparing a vitamin D compound and an intermediate thereof, comprising the step of:

(a) mixing a ketone or aldehyde, a Wittig reagent, and a base; or (b) mixing a ketone or aldehyde and a Wittig reagent, and then adding a base to the resulting mixture.

Step (b) may be performed in one pot.

In this process, the vitamin D compound is preferably a compound of general formula (I):

[formula 3]

(I)

wherein $R_1$ and $R_2$ independently represent a hydrogen atom; a straight or branched hydrocarbon optionally containing one or more double or triple bonds and optionally containing an intervening oxygen, nitrogen, phosphorous, boron or sulfur atom and optionally substituted; or a cyclic hydrocarbon optionally containing one or more double bonds and optionally containing an intervening oxygen, nitrogen, phosphorous, boron or sulfur atom and optionally substituted; or $R_1$ and $R_2$ are joined to form a cyclic hydrocarbon optionally containing one or more double bonds and optionally containing an intervening oxygen, nitrogen, phosphorous, or sulfur atom and optionally substituted; with the proviso that $R_1$ and $R_2$ do not simultaneously represent a hydrogen atom; and $R_3$ represents a straight or branched hydrocarbon optionally containing one or more double or triple bonds and optionally substituted; or a cyclic hydrocarbon optionally containing one or more double bonds and optionally substituted;

or a salt thereof.

In general formula (I), $R_1$ and $R_2$ preferably independently represent a hydrogen atom; a C1-C30 straight or branched hydrocarbon optionally containing one or more double or triple bonds and optionally containing an intervening oxygen, nitrogen, or sulfur atom; a C3-C15 cyclic hydrocarbon optionally containing one or more double bonds; a C6-C18 aryl; or a 3- to 15-membered heterocycle optionally containing one or more hetero atoms selected from oxygen, nitrogen and sulfur and optionally containing one or more double bonds; where these straight or branched hydrocarbon, cyclic hydrocarbon, aryl and heterocycle may be substituted by one or more $R_a$s; with the proviso that $R_1$ and $R_2$ do not simultaneously represent a hydrogen atom; or $R_1$ and $R_2$ are joined to form a C3-C15 cyclic hydrocarbon optionally containing one or more double bonds, or a C6-C18 aryl, or a 3- to 15-membered heterocycle containing one or more hetero atoms selected from oxygen, nitrogen and sulfur and optionally containing one or more double bonds, where these cyclic hydrocarbon, aryl and heterocycle may be substituted by one or more $R_a$s;

$R_3$ preferably represents a C3-C10 cyclic hydrocarbon optionally containing one or more double bonds and optionally substituted by one or more $R_a$s;

$R_a$ preferably represents hydroxy, cyano, carbonyl, carboxyl, ester, amide, halogen, nitro, amino, phosphorous acid, phosphoric acid, phosphoric ester, sulfonic acid, sulfonic ester, sulfonamide, thiol, =O, =CH$_2$, a C1-C15 straight or branched hydrocarbon optionally containing one or more double or triple bonds and optionally containing an intervening oxygen or sulfur atom, a C1-C6 acyloxy, a C3-C15 cyclic hydrocarbon optionally containing one or more double bonds, a C6-C14 aryl, or a 3- to 15-membered heterocycle containing one or more hetero atoms selected from oxygen, nitrogen and sulfur and optionally containing one or more double bonds, where these ester, amide, straight or branched hydrocarbon, cyclic hydrocarbon, aryl and heterocycle themselves may be substituted by one or more $R_b$s; and $R_b$ preferably represents halogen, =O, hydroxy, a C1-C6 acyloxy, a C1-C6 straight or branched hydrocarbon optionally containing one or more double or triple bonds, a C3-C15 cyclic hydrocarbon optionally containing one or more double bonds, or a C6-C14 aryl, or a 3- to 15-membered heterocycle containing one or more hetero atoms selected from oxygen, nitrogen and sulfur and optionally containing one or more double bonds, where these straight or branched hydrocarbon, cyclic hydrocarbon, aryl and heterocycle themselves may be substituted by one or more groups selected from halogen, =O, hydroxy, a C1-C6 straight or branched haloalkyl and a C1-C6 straight or branched hydroxyalkyl.

In general formula (I), $R_1$ and $R_2$ may be joined to form a bicyclo[4.3.0]nonanyl substituted by one or more $R_a$s or a bicyclo[4.3.0]nonenyl substituted by one or more $R_a$s.

In general formula (I), $R_3$ may represent a cyclohexanyl substituted by one or more $R_a$s or a cyclohexenyl substituted by one or more $R_a$s.

The compound of general formula (I) preferably has vitamin D activity or antagonist activity against vitamin D.

Alternatively, in the above process, the vitamin D compound may be of general formula (V):

[formula 4]

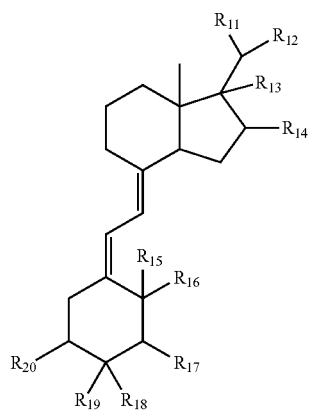

(V)

wherein $R_{11}$ and $R_{12}$ independently represent a hydrogen atom, or a C1-C30 straight or branched hydrocarbon optionally containing one or more double or triple bonds and optionally containing an intervening oxygen, nitrogen, or sulfur atom and optionally substituted by one or more $R_c$s, with the proviso that $R_{11}$ and $R_{12}$ do not simultaneously represent a hydrogen atom;

$R_{13}$ and $R_{14}$ simultaneously represent a hydrogen atom, or $R_{13}$ and $R_{14}$ are joined to form a single bond;

$R_{15}$ and $R_{16}$ simultaneously represent a hydrogen atom, or $R_{15}$ and $R_{16}$ are joined to form =CH$_2$;

$R_{17}$ represents halogen or hydroxy;

$R_{18}$ and $R_{19}$ independently represent a hydrogen atom, or a C1-C30 straight or branched hydrocarbon optionally containing one or more double or triple bonds and optionally containing an intervening oxygen, nitrogen, or sulfur atom and optionally substituted by one or more $R_c$s, or $R_{18}$ and $R_{19}$ are joined to form =O, =CH$_2$, a C3-C8 spiro hydrocarbon optionally containing one or more double bonds and optionally substituted by one or more $R_c$s, or a 3- to 15-membered spiro heterocycle containing one or more hetero atoms selected from oxygen, nitrogen and sulfur and optionally containing one or more double bonds and optionally substituted by one or more $R_c$s;

$R_c$ represents hydroxy, cyano, carbonyl, carboxyl, ester, amide, halogen, nitro, amino, phosphorous acid, phosphoric acid, phosphoric ester, sulfonic acid, sulfonic ester, sulfonamide, thiol, =O, =CH$_2$, a C1-C15 straight or branched hydrocarbon optionally containing one or more double or triple bonds and optionally containing an intervening oxygen or sulfur atom, a C1-C6 acyloxy, a C3-C15 cyclic hydrocarbon optionally containing one or more double bonds, a C6-C14 aryl, or a 3- to 15-membered heterocycle containing one or more hetero atoms selected from oxygen, nitrogen and sulfur and optionally containing one or more double bonds, where these ester, amide, straight or branched hydrocarbon, cyclic hydrocarbon, aryl and heterocycle themselves may be substituted by one or more $R_d$s;

$R_d$ represents halogen, =O, hydroxy, a C1-C6 acyloxy, a C1-C6 straight or branched hydrocarbon optionally containing one or more double or triple bonds, a C3-C15 cyclic hydrocarbon optionally containing one or more double bonds, a C6-C14 aryl, or a 3- to 15-membered heterocycle containing one or more hetero atoms selected from oxygen, nitrogen and sulfur and optionally containing one or more double bonds, where these straight or branched hydrocarbon, cyclic hydrocarbon, aryl and heterocycle themselves may be substituted by one or more groups selected from halogen, =O, hydroxy, a C1-C6 straight or branched haloalkyl and a C1-C6 straight or branched hydroxyalkyl; and $R_{20}$ represents halogen or hydroxy;

or a salt thereof.

The compound of formula (V) preferably has vitamin D activity or antagonist activity against vitamin D.

In the above process, the vitamin D compound may be a compound or a salt thereof which has a partial structure represented by formula (VI) or (VII). Preferably, it has vitamin D activity or antagonist activity against vitamin D.

[formula 5]

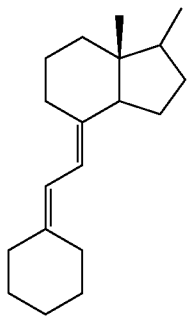

(VI)

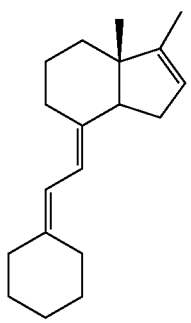

(VII)

According to the process of the present invention, an extremely low temperature such as −78° C. is not required, and vitamin D compounds and their intermediates can be synthesized under conditions such as, e.g., about −20° C. or less or room temperature.

According to the process of the present invention, the possibility of moisture inclusion during the preparation of vitamin D compounds and their intermediates can be reduced by performing the reactions in one pot. By adopting such a milder temperature condition, a moisture inclusion due to condensation or the like can also be prevented.

According to the process of the present invention, vitamin D compounds and their intermediates can be obtained without excessively using a Wittig reagent or a ketone or aldehyde.

PREFERRED EMBODIMENTS OF THE INVENTION

More specific embodiments of the present invention and procedures for carrying out the present invention are described below.

As used herein, the "vitamin D compound" refers to a compound that binds to a vitamin D receptor in vivo to induce vitamin D activity or antagonist activity against vitamin D. Such "vitamin D compounds" include e.g., the compounds represented by general formulae (I) and (V) described above. Alternative examples include compounds having a structure represented by formula (VI) or (VII) as their partial structure.

The "vitamin D activity" refers to an activity induced by binding to a vitamin D receptor in vivo to regulate the expression of genes such as parathyroid hormone, vitamin D-1a-hydroxylase, and osteocalcin genes. Specifically, it means antirachitic activity, calcium metabolism regulation, osteogenesis, cell differentiation induction, cell growth regulation, etc. Methods for detecting vitamin D activity include detection of induction of HL-60 differentiation, reporter gene assays, etc.

The "antagonist activity against vitamin D" refers to an activity induced by binding to a vitamin D receptor in vivo to inhibit the activity induced by an endogenous vitamin D. Methods for detecting antagonist activity against vitamin D include detection of induction of HL-60 differentiation, reporter gene assays, etc.

When one of $R_1$ and $R_2$ in general formula (I) is a hydrogen atom, the other preferably represents a C1-C30, more preferably C1-C20, most preferably C8-C14 straight or branched hydrocarbon optionally containing one or more double or triple bonds and optionally containing an intervening oxygen, nitrogen, or sulfur atom and optionally substituted; or a C3-C15, preferably C3-C8, more preferably C4-C7 cyclic hydrocarbon optionally containing one or more double bonds and optionally substituted. These straight or branched hydrocarbon and cyclic hydrocarbon may have one or more substituents selected from carbonyl, carboxyl, ester such as methyl ester, ethyl ester and propyl ester, amide such as methyl amide, ethyl amide and propyl amide, halogen, nitro, amino, phosphorous acid, phosphoric acid, phosphoric ester, sulfonic acid, sulfonic ester, sulfonamide, thiol halogen, hydroxy, =O (oxo), =CH$_2$ (methylene), a C1-C6 acyloxy optionally substituted by one or more substituents selected from hydroxy and halogen, a C1-C15 straight or branched hydrocarbon optionally substituted by one or more substituents selected from hydroxy and halogen and optionally containing one or more double or triple bonds and optionally containing an intervening oxygen or sulfur atom, a C3-C15 cyclic hydrocarbon optionally substituted by one or more substituents selected from hydroxy and halogen and optionally containing one or more double bonds, a C6-C14 aryl optionally substituted by one or more substituents selected from hydroxy and halogen, and a 3- to 15-membered heterocycle containing one or more hetero atoms selected from oxygen, nitrogen and sulfur and optionally containing one or more double bonds, etc. A C1-C6 straight or branched alkyl optionally substituted by one or more substituents selected from hydroxy and halogen is an especially preferred substituent.

In general formula (I), $R_1$ and $R_2$ are preferably joined to form a C3-C15, preferably C6-C12 cyclic hydrocarbon optionally containing one or more double bonds and optionally substituted, more preferably bicyclo[4.3.0]nonanyl or bicyclo[4.3.0]nonenyl. This cyclic hydrocarbon may be substituted by one or more groups selected from carbonyl, carboxyl, ester such as methyl ester, ethyl ester and propyl ester, amide such as methyl amide, ethyl amide and propyl amide, halogen, nitro, amino, phosphorous acid, phosphoric acid, phosphoric ester, sulfonic acid, sulfonic ester, sulfonamide, thiol halogen, hydroxy, =O, =CH$_2$, a C1-C6 acyloxy, a C1-C15 straight or branched hydrocarbon optionally containing one or more double or triple bonds and optionally containing an intervening oxygen or sulfur atom, a C3-C15 cyclic hydrocarbon optionally containing one or more double bonds, a C6-C14 aryl, and a 3- to 15-membered heterocycle containing one or more hetero atoms selected from oxygen, nitrogen and sulfur and optionally containing one or more double bonds. These substituents themselves may be substituted by one or more groups selected from halogen, hydroxy, =O, a C1-C6 acyloxy, a C1-C6 straight or branched hydrocarbon, a C3-6 cyclic hydrocarbon, a C6-C10 aryl optionally substituted by a C1-6 straight or branched hydroxyalkyl, and a 3- to 8-membered heterocycle optionally substituted by =O and containing one or more hetero atoms selected from oxygen, nitrogen and sulfur and optionally containing one or more double bonds.

In general formula (I), $R_3$ preferably represents a cyclic hydrocarbon optionally containing one or more double bonds and optionally substituted, more preferably a C3-C10 cyclic hydrocarbon optionally containing one or more double bonds and optionally substituted, most preferably cyclohexanyl or cyclohexenyl. This cyclic hydrocarbon may be substituted by one or more groups selected from carbonyl, carboxyl, ester such as methyl ester, ethyl ester and propyl ester, amide such as methyl amide, ethyl amide and propyl amide, halogen, nitro, amino, phosphorous acid, phosphoric acid, phosphoric ester, sulfonic acid, sulfonic ester, sulfonamide, thiol halogen, hydroxy, =O, =CH$_2$, a C1-C6 acyloxy, a C1-C15 straight or branched hydrocarbon optionally containing one or more double or triple bonds and optionally containing an intervening oxygen or sulfur atom, a C3-C15 cyclic hydrocarbon optionally containing one or more double bonds, a C6-C14 aryl, and a 3- to 15-membered heterocycle containing one or more hetero atoms selected from oxygen, nitrogen and sulfur and optionally containing one or more double bonds. These substituents themselves may be substituted by one or more groups selected from halogen, hydroxy, =O, a C1-C6 acyloxy, a C1-C6 straight or branched hydrocarbon, a C3-6 cyclic hydrocarbon, a C6-C10 aryl optionally substituted by a C1-6 straight or branched hydroxyalkyl, and a 3- to 8-membered heterocycle optionally substituted by =O and containing one or more hetero atoms selected from oxygen, nitrogen and sulfur and optionally containing one or more double bonds.

In the definition of $R_{11}$ and $R_{12}$ in general formula (V), the "C1-C30 straight or branched hydrocarbon optionally containing one or more double or triple bonds and optionally containing an intervening oxygen, nitrogen, or sulfur atom" preferably contains 1 to 16 carbon atoms.

$R_{11}$ and $R_{12}$ may have one or more substituents selected from carbonyl, carboxyl, ester such as methyl ester, ethyl ester and propyl ester, amide such as methyl amide, ethyl amide and propyl amide, halogen, nitro, amino, phosphorous acid, phosphoric acid, phosphoric ester, sulfonic acid, sulfonic ester, sulfonamide, thiol halogen, hydroxy, =O, =CH$_2$, a C1-C6 acyloxy, a C1-C15 straight or branched hydrocarbon optionally containing one or more double or triple bonds and optionally containing an intervening oxygen or sulfur atom, a C3-C15 cyclic hydrocarbon optionally containing one or more double bonds, a C6-C14 aryl, and a 3- to 15-membered heterocycle containing one or more hetero atoms selected from oxygen, nitrogen and sulfur and optionally containing one or more double bonds. These acyloxy, straight or branched hydrocarbon, cyclic hydrocarbon, aryl and heterocycle themselves may have one or more substituents selected from hydroxy and halogen. When one of $R_{11}$ and $R_{12}$ is a hydrogen atom, the other preferably has one or more substituents shown above, more preferably one or more substituents selected from hydroxy and halogen.

$R_{17}$ represents halogen such as fluorine, iodine, chlorine and bromine, or hydroxy, preferably hydroxy.

In the definition of $R_{18}$ and $R_{19}$, the "C1-C30 straight or branched hydrocarbon optionally containing one or more double or triple bonds and optionally containing an intervening oxygen, nitrogen, or sulfur atom and optionally substituted by one or more $R_aS$" preferably contains 1 to 16 carbon atoms, more preferably 1 to 6 carbon atoms, still more preferably 1 to 4 carbon atoms. The intervening atom contained in this straight or branched hydrocarbon is preferably an oxygen atom.

$R_{18}$ and $R_{19}$ may have one or more substituents selected from carbonyl, carboxyl, ester such as methyl ester, ethyl ester and propyl ester, amide such as methyl amide, ethyl amide and propyl amide, halogen, nitro, amino, phosphorous acid, phosphoric acid, phosphoric ester, sulfonic acid, sulfonic ester, sulfonamide, thiol halogen, hydroxy, =O, =CH$_2$, a C1-C6 acyloxy, a C1-C15 straight or branched hydrocarbon optionally containing one or more double or triple bonds and optionally containing an intervening oxygen or sulfur atom, a C3-C15 cyclic hydrocarbon optionally containing one or more double bonds, a C6-C14 aryl, and a 3- to 15-membered heterocycle containing one or more hetero atoms selected from oxygen, nitrogen and sulfur and optionally containing one or more double bonds. These acyloxy, straight or branched hydrocarbon, cyclic hydrocarbon, aryl and heterocycle themselves may have one or more substituents selected from hydroxy and halogen. When one of $R_{18}$ and $R_{19}$ is a hydrogen atom, the other preferably has one or more substituents shown above, more preferably one or more substituents selected from hydroxy and halogen.

$R_{18}$ and $R_{19}$ may simultaneously represent a hydrogen atom, and at least one of them is preferably a hydrogen atom.

$R_{20}$ represents halogen such as fluorine, iodine, chlorine and bromine, or hydroxy, preferably hydroxy.

The "ketone" refers to a compound of general formula (II):

wherein $R_5$ and $R_6$ independently represent a straight or branched hydrocarbon optionally containing one or more double or triple bonds and optionally containing an intervening oxygen, nitrogen, phosphorous, boron or sulfur atom and optionally substituted; or a cyclic hydrocarbon optionally containing one or more double bonds and optionally containing an intervening oxygen, nitrogen, phosphorous, boron or sulfur atom and optionally substituted; or $R_5$ and $R_6$ are joined to form a cyclic hydrocarbon optionally containing one or more double bonds and optionally containing an intervening oxygen, nitrogen, phosphorous, boron or sulfur atom and optionally substituted; or a salt thereof.

In general formula (II), $R_5$ and $R_6$ are preferably joined to form a C3-C15 cyclic hydrocarbon optionally containing one or more double bonds, more preferably a bicyclo[4.3.0]nonanyl having one or more substituents or a bicyclo[4.3.0]nonenyl having one or more substituents.

The substituents on $R_5$ and $R_6$ in general formula (II) include carbonyl, carboxyl, ester such as methyl ester, ethyl ester and propyl ester, amide such as methyl amide, ethyl amide and propyl amide, halogen, nitro, amino, phosphorous acid, phosphoric acid, phosphoric ester, sulfonic acid, sulfonic ester, sulfonamide, thiol halogen, hydroxy, =O, =CH$_2$, a C1-C6 acyloxy, a C1-C15 straight or branched hydrocarbon optionally containing one or more double or triple bonds and optionally containing an intervening oxygen or sulfur atom, a C3-C15 cyclic hydrocarbon optionally containing one or more double bonds, a C6-C14 aryl, and a 3- to 15-membered heterocycle containing one or more hetero atoms selected from oxygen, nitrogen and sulfur and optionally containing one or more double bonds. These substituents themselves may be substituted by one or more groups selected from halogen, hydroxy, =O, a C1-C6 acyloxy, a C1-C6 straight or branched hydrocarbon, a C3-6 cyclic hydrocarbon, a C6-C10 aryl optionally substituted by a C1-6 straight or branched hydroxyalkyl, and a 3- to 8-membered heterocycle optionally substituted by =O and containing one or more hetero atoms selected from oxygen, nitrogen and sulfur and optionally containing one or more double bonds. $R_5$ and $R_6$ can contain one or more substituents which may be protected by a protective group, as appropriate.

In the present invention, octahydroindene-4-one derivatives and the like are preferably used as ketones.

The "aldehyde" refers to a compound of general formula (III):

wherein $R_7$ represents a straight or branched hydrocarbon optionally containing one or more double or triple bonds and optionally containing an intervening oxygen, nitrogen, phosphorous, boron or sulfur atom and optionally substituted; or a cyclic hydrocarbon optionally containing one or more double bonds and optionally containing an intervening oxygen, nitrogen, phosphorous, boron or sulfur atom and optionally substituted; or a salt thereof.

In general formula (III), $R_7$ preferably represents a C1-C30, preferably C1-C20, more preferably C8-C14 straight or branched hydrocarbon optionally containing one or more double or triple bonds and optionally containing an intervening oxygen, nitrogen, or sulfur atom and optionally substituted; or a C3-C15, preferably C3-C8, more preferably C4-C7 cyclic hydrocarbon optionally containing one or more double bonds and optionally substituted. Substituents on these straight or branched hydrocarbon and cyclic hydrocarbon include carbonyl, carboxyl, ester such as methyl ester, ethyl ester and propyl ester, amide such as methyl amide, ethyl amide and propyl amide, halogen, nitro, amino, phosphorous acid, phosphoric acid, phosphoric ester, sulfonic acid, sulfonic ester, sulfonamide, thiol halogen, hydroxy, =O (oxo), =CH$_2$ (methylene), a C1-C6 acyloxy optionally substituted by one or more substituents selected from hydroxy and halogen, a C1-C15 straight or branched hydrocarbon optionally containing one or more substituents selected from hydroxy and halogen and optionally containing one or more double or triple bonds and optionally containing an intervening oxygen or sulfur atom, a C3-C15 cyclic hydrocarbon optionally containing one or more substituents selected from hydroxy and halogen and optionally containing one or more double bonds, a C6-C14 aryl optionally containing one or more substituents selected from hydroxy and halogen, and a 3- to 15-membered heterocycle containing one or more hetero atoms selected from oxygen, nitrogen and sulfur and optionally containing one or more double bonds. $R_7$ can contain one or more substituents which may be protected by a protective group, as appropriate.

Wittig reagents include phosphonium salt derivatives, phosphonic ester derivatives, and phosphine oxide derivatives. In the present invention, phosphine oxide derivatives are preferred, and allylphosphine oxide derivatives are more preferred.

Allylphosphine oxide derivatives are the compounds of general formula (IV):

[formula 6]

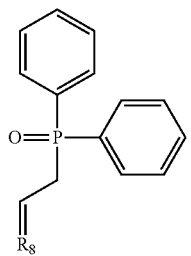

(IV)

wherein $R_8$ represents a straight or branched hydrocarbon optionally containing one or more double or triple bonds, or a cyclic hydrocarbon optionally containing one or more double bonds and optionally substituted; or a salt thereof.

$R_8$ preferably represents a cyclic hydrocarbon optionally containing one or more double bonds and optionally substituted, more preferably a C3-C10 cyclic hydrocarbon optionally containing one or more double bonds and optionally substituted, still more preferably an optionally substituted cyclohexanyl or an optionally substituted cyclohexenyl.

Substituents on $R_8$ in general formula (IV) include carbonyl, carboxyl, ester such as methyl ester, ethyl ester and propyl ester, amide such as methyl amide, ethyl amide and propyl amide, halogen, nitro, amino, phosphorous acid, phosphoric acid, phosphoric ester, sulfonic acid, sulfonic ester, sulfonamide, thiol halogen, hydroxy, =O, =CH$_2$, a C1-C6 acyloxy, a C1-C15 straight or branched hydrocarbon optionally containing one or more double or triple bonds and optionally containing an intervening oxygen or sulfur atom, a C3-C15 cyclic hydrocarbon optionally containing one or more double bonds, a C6-C14 aryl, and a 3- to 15-membered heterocycle containing one or more hetero atoms selected from oxygen, nitrogen and sulfur and optionally containing one or more double bonds. These substituents themselves may be substituted by one or more groups selected from halogen, hydroxy, =O, a C1-C6 acyloxy, a C1-C6 straight or branched hydrocarbon, a C3-6 cyclic hydrocarbon, a C6-C10 aryl optionally substituted by a C1-6 straight or branched hydroxyalkyl, and a 3- to 8-membered heterocycle optionally substituted by =O and containing one or more hetero atoms selected from oxygen, nitrogen and sulfur and optionally containing one or more double bonds. $R_8$ can contain one or more substituents which may be protected by a protective group, as appropriate.

In the present invention, the "intermediate of a vitamin D compound" refers to an intermediate of the vitamin D compound as defined above, and examples include vitamin D compounds having a protective group on each functional group. Specific examples are the compounds of general formula (I) wherein any one of $R_1$, $R_2$, $R_3$ and substituents thereon if any is protected by a protective group and the compounds of general formula (V) wherein any one of $R_{11}$, $R_{12}$, $R_{17}$, $R_{18}$, $R_{19}$, $R_{20}$ and substituents thereon if any is protected by a protective group.

Protective groups on $R_1$, $R_2$, $R_3$, $R_5$, $R_6$, $R_7$, $R_8$, $R_{11}$, $R_{12}$, $R_{17}$, $R_{18}$, $R_{19}$, $R_{20}$ and substituents thereon if any in general formulae (I), (II), (III), (IV) and (V) include, but not limited to, acyl, substituted silyl and substituted or unsubstituted alkyl groups, preferably acyl and substituted silyl groups. Examples of acyl groups include acetyl, benzoyl, substituted acetyl and substituted benzoyl groups, and acyl carbonate and acyl carbamate groups, preferably acetyl. Examples of substituents on acetyl and benzoyl groups include halogen atoms, and alkyl, alkenyl and aryl groups, preferably fluorine and chlorine atoms, and methyl, phenyl and ethylidene groups. Preferred examples of substituted acetyl groups include chloroacetyl, trifluoroacetyl, pivaloyl and crotonoyl groups. Preferred examples of substituted benzoyl groups include p-phenylbenzoyl and 2,4,6-trimethyl benzoyl groups. Examples of substituted silyl groups include trimethylsilyl, triethylsilyl (TMS), triisopropylsilyl, tert-butyldimethylsilyl (TBS) and tert-butyldiphenylsilyl groups, preferably triethylsilyl (TMS) and tert-butyldimethylsilyl (TBS) groups. Examples of substituted or unsubstituted alkyl groups include methyl, methoxymethyl, methylthiomethyl, tert-butylthiomethyl, benzyloxymethyl, p-methoxybenzyloxymethyl, 2-methoxyethoxymethyl, tetrahydropyranyl, tert-butyl, allyl, benzyl, p-methoxybenzyl, and o- or p-nitrobenzyl groups.

Bases include, e.g., lithium hexamethyldisilazide, sodium hexamethyldisilazide, potassium hexamethyldisilazide, lithium diisopropylamide, lithium azide, sodium azide, sodium hydride, potassium hydride, lithium methoxide, lithium ethoxide, lithium tert-butoxide, sodium methoxide, sodium ethoxide, sodium tert-butoxide, potassium methoxide, potassium ethoxide, potassium tert-butoxide, sodium hydride-dimethyl sulfide, potassium carbonate, sodium carbonate, tert-butyl lithium, n-butyl lithium, methyl lithium, ethyl lithium, phenyl lithium, Triton B, lithium hydroxide, sodium hydroxide, potassium hydroxide, sodium iodide-1,8-diazabicyclo-[5.4.0]-undec-7-ene, lithium chloride-1,8-diazabicyclo-[5.4.0]-undec-7-ene. Preferred are lithium hexamethyldisilazide, lithium diisopropylamide, n-butyl lithium, sodium hexamethyldisilazide, potassium hexamethyldisilazide, and potassium tert-butoxide. Lithium hexamethyldisilazide is more preferred.

The salt of the compound represented by general formula (I), the salt of the compound represented by general formula (V), or the salt of the compound having a structure represented by formula (VI), (VII), (VIII) or (IX) as its partial structure is preferably a pharmacologically acceptable salt, e.g. a salt with an inorganic base, a salt with an organic base, a salt with a basic or acidic amino acid. Inorganic bases include alkali metals such as sodium and potassium, and alkali earth metals such as calcium and magnesium; organic bases include e.g., trimethylamine, triethylamine, pyridine, picoline, N,N'-dibenzylethylenediamine, and diethanolamine; inorganic acids include hydrochloric acid, hydrobromic acid, hydroiodic acid, phosphoric acid, nitric acid, and sulfuric acid; organic acids include formic acid, acetic acid, trifluoroacetic acid, oxalic acid, tartaric acid, fumaric acid, maleic acid, methanesulfonic acid, benzenesulfonic acid, p-toluenesulfonic acid, and citric acid; and basic or acidic amino acids include e.g., arginine, lysine, aspartic acid, and glutamic acid.

According to the present invention, the process for preparing a vitamin D compound or its intermediate may be carried out by initially mixing a ketone and a Wittig reagent and then adding a base to the resulting mixture, as shown below.

A ketone and a Wittig reagent are added into a reaction vessel, and mixed at, e.g., room temperature. The ketone and Wittig reagent may be individually dissolved and then mixed. Different solvents may be used for the individual dissolution. Solvents having no influence on the reaction are preferably used. Examples include hydrocarbons such as benzene, toluene, xylene and hexane; ethers such as ethyl ether, tetrahydrofuran, dioxane and t-butyl methyl ether; and mixed solvents thereof. Benzene or toluene is preferably used because they allow water to be removed from the substrates by azeotropic procedure.

To the resulting mixture of the ketone and the Wittig reagent is added a base at room temperature or below, e.g., 20° C., 15° C., 10° C., 5° C., 0° C., −10° C., −15° C., −20° C., or below. For example, the mixture of the ketone and the Wittig reagent is evaporated to dryness, and the residue is reconstituted in another solvent preferably in a nitrogen atmosphere, and the resulting solution is cooled to room temperature or below, e.g., −78° C. to room temperature, preferably about −20° C. to room temperature, more preferably about −20° C., and then a base dissolved in a suitable solvent is added preferably slowly in portions. The solvent in which the residue obtained by the evaporation of the mixture of the ketone and Wittig reagent is reconstituted or the solvent in which a base is dissolved are preferably those having no influence on the reaction. Examples of the solvents include hydrocarbons such as benzene, toluene, xylene and hexane; ethers such as ethyl ether, tetrahydrofuran, dioxane and t-butyl methyl ether; and mixed solvents thereof. For example, tetrahydrofuran and dioxane are preferably used.

Then, the resulting mixture is warmed to room temperature to 60° C., preferably to 50° C., stirred, and then evaporated, and the residue is purified by chromatography or the like.

According to the present invention, the process for preparing a vitamin D compound or its intermediate may also be carried out by initially mixing an aldehyde and a Wittig reagent and then adding a base to the resulting mixture, as shown below.

A solution of an aldehyde and a Wittig reagent or a solution of only a Wittig reagent in a solvent is added into a reaction vessel, and mixed at, e.g., room temperature. A Wittig reagent may be dissolved in a solvent and then mixed with an aldehyde. Solvents having no influence on the reaction are preferably used. Examples include hydrocarbons such as benzene, toluene, xylene and hexane; ethers such as ethyl ether, tetrahydrofuran, dioxane and t-butyl methyl ether; and mixed solvents thereof. Benzene or toluene is preferably used because they allow water to be removed from the substrates by azeotropic procedure. Alternatively, the solution of a Wittig reagent may be evaporated to dryness, and then an aldehyde may be mixed with the resulting residue preferably in a nitrogen atmosphere.

To the resulting mixture of the aldehyde and the Wittig reagent is added a base at room temperature or below, e.g., 20° C., 15° C., 10° C., 5° C., 0° C., −10° C., −15° C., −20° C., or below. For example, the mixture of the aldehyde and the Wittig reagent is evaporated to dryness, and the residue is reconstituted in another solvent preferably in a nitrogen atmosphere, and the resulting solution is cooled to room temperature or below, e.g., −78° C. to room temperature, preferably about −20° C. to room temperature, more preferably about −20° C., and then a base dissolved in a suitable solvent is added preferably slowly in portions. The solvent in which the residue obtained by the evaporation of the mixture of the aldehyde and Wittig reagent is reconstituted or the solvent in which a base is dissolved are preferably those having no influence on the reaction. Examples of the solvents include hydrocarbons such as benzene, toluene, xylene and hexane; ethers such as ethyl ether, tetrahydrofuran, dioxane and t-butyl methyl ether; and mixed solvents thereof. For example, tetrahydrofuran and dioxane are preferably used.

Then, the resulting mixture is warmed to room temperature to 60° C., preferably to 50° C., stirred, and then evaporated, and the residue is purified by chromatography or the like.

According to the process described above, from the step of mixing a ketone or aldehyde and a Wittig reagent to the step of adding a base to the resulting mixture can be performed in the same reaction vessel.

When any protective group is present on the hydroxy group or the like of the resulting purified product, it can be removed by any method described in documents, e.g., by using tetraammonium fluoride (Bioorg. Med. Chem. 9 (2001) 403), or using AG 50W-X4 (Steroids, 67, 2002, 247), to give the intended vitamin D compound.

According to the process for preparing a vitamin D compound or its intermediate of the present invention, a ketone or aldehyde, a Wittig reagent, and a base may also be mixed, as shown below.

A ketone or aldehyde, a Wittig reagent, and a base are mixed directly or after they are dissolved in suitable solvents such as tetrahydrofuran and dioxane, by adding into a reaction vessel at individually suitable rates, e.g., at constant rates, at −78° C. to room temperature, preferably −20° C. to room temperature, more preferably −20° C., then the resulting mixture is warmed to, e.g., 50° C. or room temperature with stirring, evaporated, and the residue is purified by chromatography or the like.

According to the process described above, from the step of mixing a ketone or aldehyde and a Wittig reagent to the step of adding a base to the resulting mixture can be performed in the same reaction vessel.

When any protective group is present on the hydroxy group or the like of the resulting purified product, it can be removed by any method described in documents, e.g., by using tetraammonium fluoride (Bioorg. Med. Chem. 9 (2001) 403), or using AG 50W-X4 (Steroids, 67, 2002, 247), to give the intended vitamin D compound.

Vitamin D compounds 1 to 22 shown in Tables 1 to 6 below can be synthesized by the processes described above. The Wittig reagents, ketones and aldehydes used as starting materials for synthesizing the vitamin D compounds shown in the tables are known compounds and can be synthesized by the methods described in the documents shown in the table.

TABLE 1

| Compound No. | Wittig reagent | Ketone | Intermediate of vitamin D compound | Vitamin D compound |
|---|---|---|---|---|
| Compound 1 | Hatakeyama S. et. al., Bioorg. Med. Chem. 9 (2001) 403 | Baggiolini G. et. al., J. Am. Chem. Soc., 104, 10, 1982, 2945 | | Fujishima T. et. al., Bioorg. Med. Chem. Lett., 8, 2000, 123 |
| Compound 2 | Hijikuro I. et.al., J. Amer. Chem. Soc. 123, 16, 2001, 3716 | Baggiolini G. et. al., J. Am. Chem. Soc., 104, 10, 1982, 2945 | | Miyamato K. et. al., Chem. Pharm. Bull. 41, 1993, 1111 |

TABLE 1-continued

| Compound No. | Wittig reagent | Ketone | Intermediate of vitamin D compound | Vitamin D compound |
|---|---|---|---|---|
| Compound 3 | Baggiolini E. et al., J. Org. Chem., 51, 1986, 3098 | Uskokovic M. R. et al., Vitamin D: Chemistry, Biology and Clinical Applications of the Steroid Hormone: Proceedings of the Tenth Workshop on Vitamin D, University of California, Riverside, Printing and Reprographics, 1997, 19 | | Uskokovic M. R. et al., Vitamin D: Chemistry, Biology and Clinical Applications of the Steroid Hormone: Proceedings of the Tenth Workshop on Vitamin D, University of California, Riverside, Printing and Reprographics, 1997, 19 |

TABLE 2

| Compound No. | Wittig reagent | Ketone or aldehyde | Intermediate of | Vitamin D compound |
|---|---|---|---|---|
| Compound 4 | Baggiolini E. et. al., J. Org. Chem., 51, 1986, 3098 | Kutner A. et. al., Vitamin D: A Pluripotent Steroid Hormone: Structural Studies, Molecular Endocrinology and Clinical Applications: Proceedings of the Ninth Workshop on Vitamin D, Walter de Gruyter, 1994, 29 | | Kutner A. et. al., Vitamin D: A Pluripotent Steroid Hormone: Structural Studies, Molecular Endocrinology and Clinical Applications: Proceedings of the Ninth Workshop on Vitamin D, Walter de Gruyter, 1994, 29 |

TABLE 2-continued

| Compound No. | Wittig reagent | Ketone or aldehyde | Intermediate of | Vitamin D compound |
|---|---|---|---|---|
| Compound 5 | 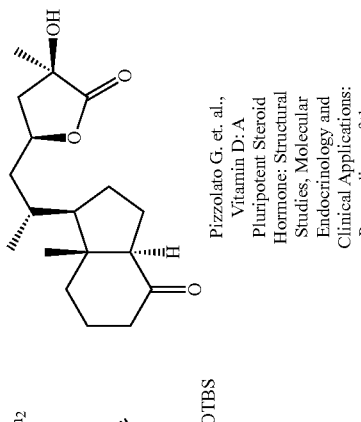 Baggiolini E. et. al., J. Org. Chem., 51, 1986, 3098 | 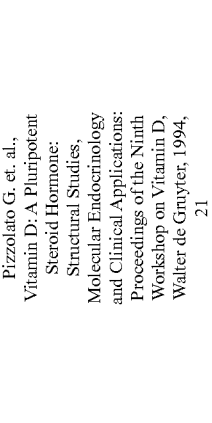 Pizzolato G. et. al., Vitamin D: A Pluripotent Steroid Hormone: Structural Studies, Molecular Endocrinology and Clinical Applications: Proceedings of the Ninth Workshop on Vitamin D, Walter de Gruyter, 1994, 21 | 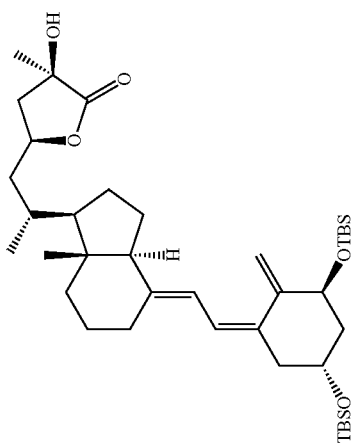 | 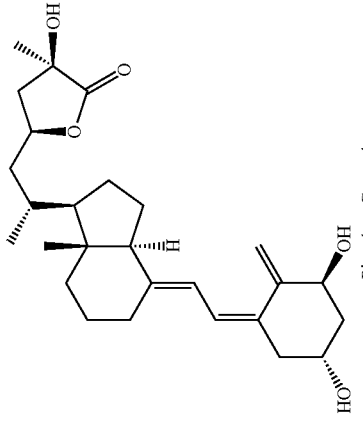 Pizzolato G. et. al., Vitamin D: A Pluripotent Steroid Hormone: Structural Studies, Molecular Endocrinology and Clinical Applications: Proceedings of the Ninth Workshop on Vitamin D, Walter de Gruyter, 1994, 21 |
| Compound 6 | 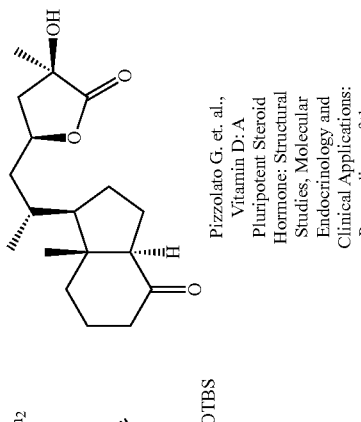 Baggiolini E. et. al., J. Org. Chem., 51, 1986, 3098 | 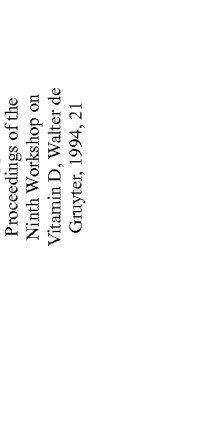 | 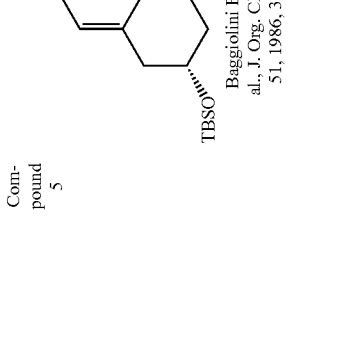 | 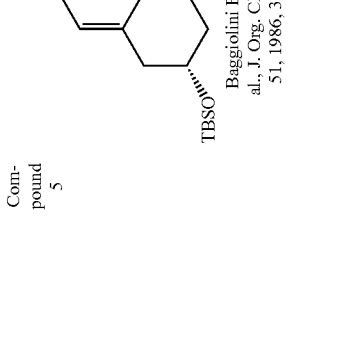 Herdick H et. Al., J. Bio. Chem., 275, 22, 16506 |

TABLE 2-continued

| Compound No. | Wittig reagent | Ketone or aldehyde | Intermediate of | Vitamin D compound |
|---|---|---|---|---|
| Compound 7 | (TBSO, OTBS, POPh₂ structure) Baggiolini E. et al., J. Org. Chem., 51, 1986, 3098 | (ketone structure with OTMS-cyclopropyl side chain) | (intermediate with OTMS, OTBS, TBSO groups) | (vitamin D compound with OH groups) Martin J. C., Tetrahedron. 43, 20, 1987, 4609 |

TABLE 3
| Compound No. | Wittig reagent | Ketone or aldehyde | Intermediate of Vitamin D compound | Vitamin D compound |
|---|---|---|---|---|
| Compound 8 | 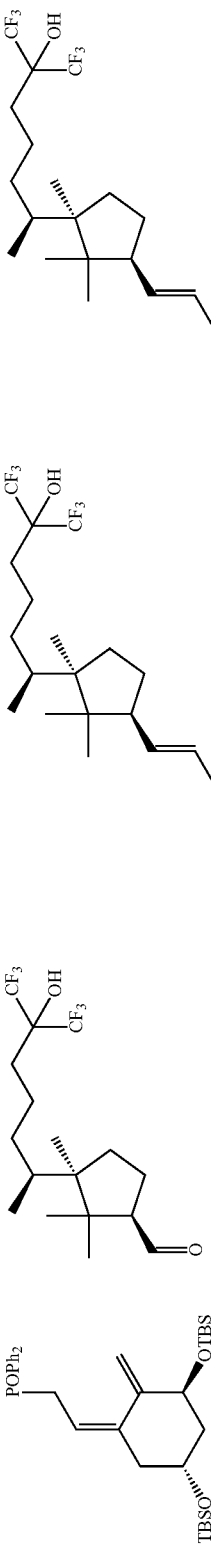 Baggiolini E. et al., J. Org. Chem., 51, 1986, 3098 |  Wu Y. et al., Bioorg. Med. Chem. Lett., 12, 2002, 1633 | 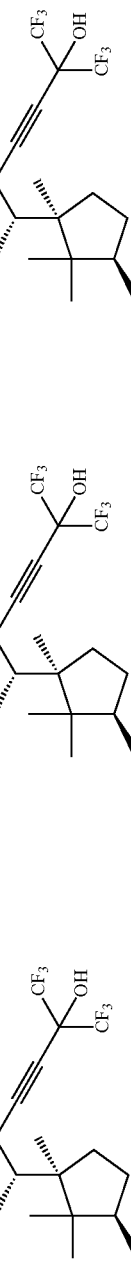 | 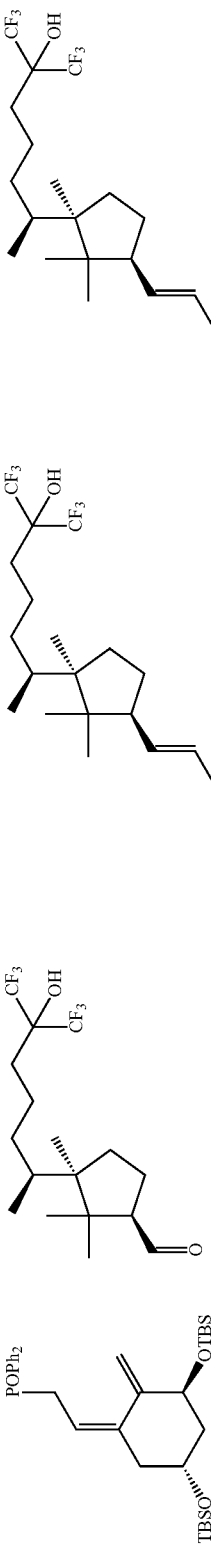 Wu Y. et al., Bioorg. Med. Chem. Lett., 12, 2002, 1633 |
| Compound 9 |  Kato P. et al., Tetrahedron Lett., 32, 52, 1991, 7663 | 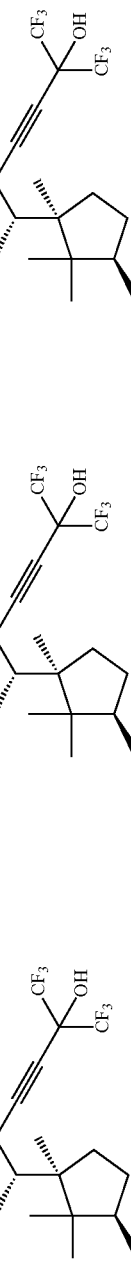 Wu Y. et al., Bioorg. Med. Chem. Lett., 12, 2002, 1633 | | Wu Y. et al., Bioorg. Med. Chem. Lett., 12, 2002, 1633 |

TABLE 3-continued
| Compound No. | Wittig reagent | Ketone or aldehyde | Intermediate of Vitamin D compound | Vitamin D compound |
|---|---|---|---|---|
| Compound 10 | 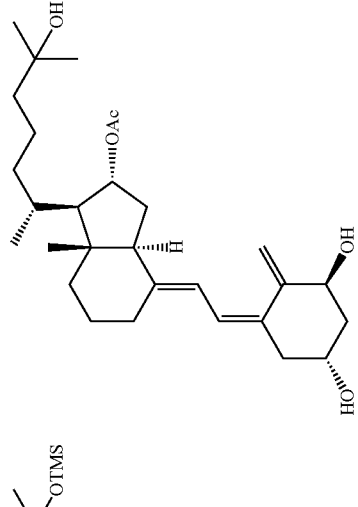 Baggiolini E. et. al., J. Org. Chem., 51, 1986, 3098 | 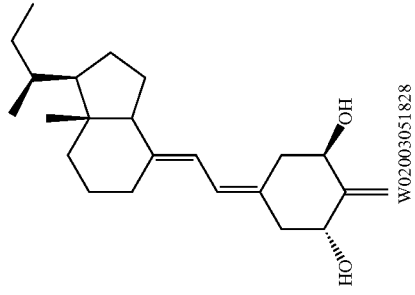 Martin J. C. et al., J. Org. Chem, 68, 2003, 1367 | 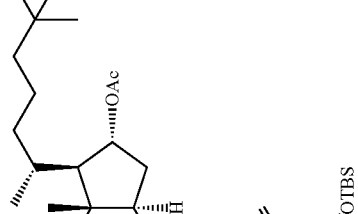 | 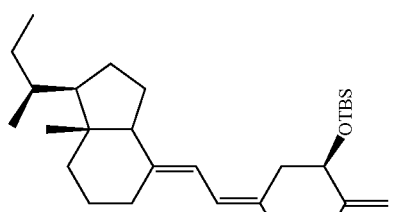 Martin J. C. et al., J. Org. Chem, 68, 2003, 1367 |
| Compound 11 | 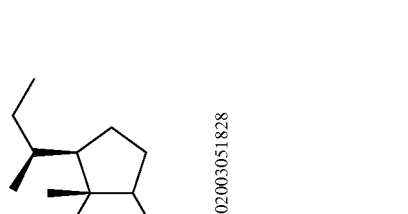 Sicinski R. et al., J. Med. Chem., 41, 23, 1998, 4662 | WO2003051828 | WO2003051828 | WO2003051828 |

TABLE 4

| Compound No. | Wittig reagent | Ketone | Intermediate of | Vitamin D Compound |
|---|---|---|---|---|
| Compound 12 | Baggiolini E. et. al., J. Org. Chem., 51, 1986, 3098 | | | Manabe K. et. al., Vitamin D: A Pluripotent Steroid Hormone: Structural Studies, Molecular Endocrinology and Clinical Applications: Proceedings of the Ninth Workshop on Vitamin D, Walter de Gruyter, 1994, 79 |
| Compound 13 | Baggiolini E. et. al., J. Org. Chem., 51, 1986, 3098 | Barrett, A. G. M. et al., J. Chem. Soc. Perkin Trans. 1, 1977, 631 | | |

TABLE 4-continued

| Compound No. | Wittig reagent | Ketone | Intermediate of | Vitamin D Compound |
|---|---|---|---|---|
| Compound 14 | Kato P. et. al., Tetrahedron Lett., 32, 52, 1991, 7663 | Baggiolini G., J. Org. Chem., 51, 16, 1986, 3098 | | |
| Compound 15 | Baggiolini E. et. al., J. Org. Chem., 51, 1986, 3098 | Kabat. M. et. al., Bioorg. Med. Chem. 6, 11, 1998, 2051 | | Chen T. C., et. al., J. Nutr. Biochem., 4, 1993, 49 |

TABLE 5
| Compound No. | Wittig reagent | Ketone or aldehyde | Intermediate of | Vitamin D Compound |
|---|---|---|---|---|
| Compound 16 | 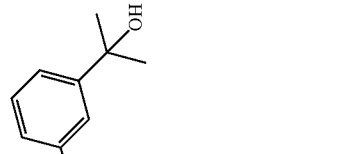 Baggiolini E. et. al., J. Org. Chem., 51, 1986, 3098 | 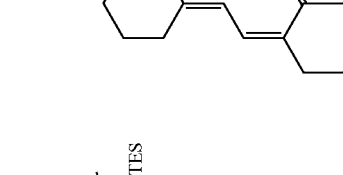 | 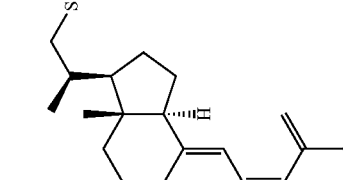 | Daehne W. et. al., Vitamin D: Chemistry, Biology and Clinical Applications of the Steroid Hormone: Proceedings of the Tenth Workshop on Vitamin D, University of California, Riverside, Printing and Reprographics, 1997, 81 |

TABLE 5-continued

| Compound No. | Wittig reagent | Ketone or aldehyde | Intermediate of | Vitamin D Compound |
|---|---|---|---|---|
| Compound 17 | Shiuey S. et. al., J. Org. Chem., 55, 1990, 243 | Baggiolini G. et. al., J. Am. Chem. Soc., 104, 10, 1982, 2945 | | Shiuey S. et. al., J. Org. Chem., 55, 1990, 243 |
| Compound 18 | Baggiolini E. et. al., J. Org. Chem., 51, 1986, 3098 | Ikeda M. et. al., Bioorg. Med. Chem., 8, 8, 2000, 2157 | Ikeda M. et. al., Bioorg. Med. Chem., 8, 8, 2000, 2157 | |

TABLE 5-continued

| Compound No. | Wittig reagent | Ketone or aldehyde | Intermediate of | Vitamin D Compound |
|---|---|---|---|---|
| Compound 19 | (structure with POPh₂, OTBS, TBSO; Kato P. et. al., Tetrahedron Lett., 32, 52, 1991, 7663) | (structure with F₃C, OTES, CF₃, and aldehyde; Hilpert H. et al., Tetrahedron, 57, 2001, 681) | (structure with F₃C, OTES, CF₃, OTBS, TBSO) | (structure with F₃C, OH, CF₃, OH, HO; Hilpert H. et al., Tetrahedron, 57, 2001, 681) |

TABLE 6
| Compound No. | Wittig reagent | Ketone | Intermediate of | Vitamin D compound |
|---|---|---|---|---|
| Compound 20 |  Baggiolini E. et. al., J. Org. Chem., 51, 1986, 3098 | 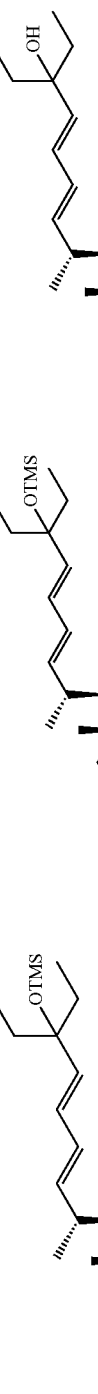 Posner G. et. al., J. Org. Chem., 62, 10, 1997, 3299 | 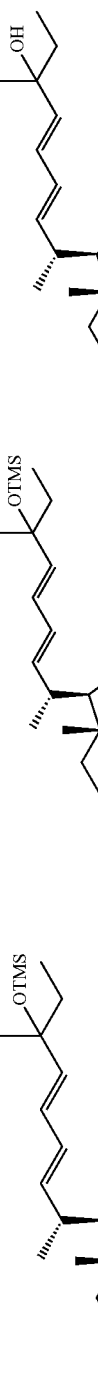 | Binderup L. et al., Vitamin D: A Pluripotent Steroid Hormone: Structural Studies, Molecular Endocrinology and Clinical Applications: Proceedings of the Ninth Workshop on Vitamin D, Walter de Gruyter, 1994, 55 |

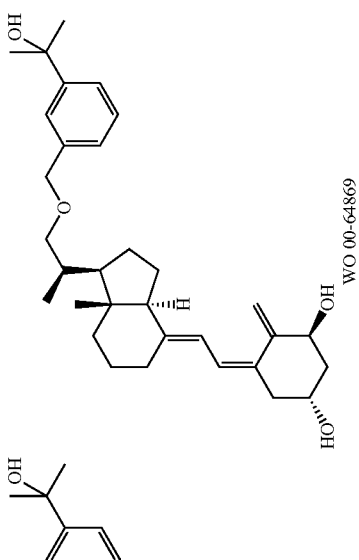

The present application claims the priority of Japanese Patent Application No. 2004-26291, which is incorporated herein by reference in its entirety.

EXAMPLES

The following examples further illustrate the present invention without, however, limiting the invention thereto.

Conditions for instrumental analyses:

$^1$H NMR analyses were performed by JMN-EX270 available from JEOL using tetramethylsilane (TMS) as an internal standard in tritiated chloroform. The following abbreviations were used to described signal multiplicity in NMR data: s=singlet: d=doublet; t=triplet; m=multiplet; arom=aromatic; br=broad signal.

UV detection was performed in ethanol by UV-1600PC available from SHIMADZU.

Example 1

A 0.3M solution of each ketone shown in Tables 7 and 8 below in benzene (66.6 μL, 20 μmol) and a 0.22 M solution of each Wittig reagent in benzene (100 μL, 22 μmol) were added into a reaction vessel, and the benzene was distilled off from the resulting mixture and the residue was dried under reduced pressure for 3 hours. The resulting residue was dissolved in 200 μL of tetrahydrofuran in a nitrogen atmosphere at room temperature, and the solution was cooled to −20° C. and then 2 μL of a 1 M solution of lithium bistrimethylsilylamide in tetrahydrofuran was added every second eleven times (22 μL, 22 μmol in total). Then, the reaction mixture was stirred at 50° C. for 16 hours. After the reaction was complete, the solvent was distilled off. All the procedures up to this point were performed in the same vessel. The resulting residue was purified by preparative TLC (Merk, silica gel 60, eluted with ethyl acetate:hexane=1:20) to give compounds A to F shown in the columns entitled "Actual and percent yields of the compound obtained" in Tables 7 and 8. Compounds A to F are intermediates of their corresponding vitamin D compounds. The Wittig reagents and ketones used as starting materials for the syntheses can be synthesized by the methods described in the documents shown in the tables.

The material data of the resulting compounds A to F are shown below.

$^1$H NMR for compound A: 0.55 (s, 3H), 1.20 (s, 6H), 2.78-2.88 (m, 1H), 4.17-4.22 (m, 1H), 4.37-4.42 (m, 1H), 4.84 (s, 1H), 5.19 (s, 1H), 6.00 (d, 1H, J=11.5Hz), 6.21 (d, 1H, J=11.5Hz).

$^1$H NMR for compound B: 0.54 (s, 3H), 1.20 (s, 6H), 4.34-4.42 (m, 2H), 4.92 (s, 1H), 4.97 (s, 1H), 5.83 (s, 1H, J=11.2Hz), 6.21 (s, 1H, J=11.2Hz).

$^1$H NMR for compound C: 0.53 (s, 3H), 1.20 (s, 6H), 4.15-4.22 (m, 1H), 4.37-4.42 (m, 1H), 4.87 (s, 1H), 5.17 (s, 1H), 6.01 (d, 1H, J=11.4Hz), 6.23 (d, 1H, J=11.4Hz).

$^1$H NMR for compound D: 0.54 (s, 3H), 0.93 (d, 3H, J=6.1Hz), 1.20 (s, 6H), 4.01-4.10 (m, 2H), 5.80 (d, 1H, J=11.3Hz), 6.16 (d, 1H, J=11.3Hz).

$^1$H NMR for compound E: 0.52 (s, 3H), 1.16 (d, 3H, J=.9Hz), 1.20 (s, 6H), 3.17-3.22 (m,1H), 3.28-3.36 (m, 1H), 3.60-3.70 (m, 1H), 4.17-4.23 (m, 1H), 4.35-4.40 (m, 1H), 4.86 (s, 1H), 5.18 (s, 1H), 6.02 (d, 1H, J=13.0Hz), 6.22 (d, 1H, J=13.0Hz).

$^1$H NMR for compound F: 0.55 (s, 3H), 1.07 (d, 3H, J=5.8Hz), 3.10-3.20 (m, 1H), 3.20-3.30 (m, 1H), 3.50-3.60 (m, 1H), 4.13-4.21 (m, 1H), 4.34-4.40 (m, 1H), 4.86 (s, 1H), 5.19 (m, 1H), 6.00 (d, 1H, J=11.0Hz), 6.24 (d, 1H, J=11.0Hz).

Compound A (12.5 mg) was dissolved in tetrahydrofuran (500 μL) at room temperature. To the resulting solution was added a 1M solution of n-tetrabutylammonium fluoride in tetrahydrofuran (200 μL) at room temperature with stirring, and stirring was continued at 60° C. for 1 hour. The reaction mixture was combined with ethyl acetate, and the organic layers were washed with water and dried over magnesium sulfate, and then the solvent was distilled off under reduced pressure, and the residue was purified by preparative TLC (Merk silica gel 60, eluted with ethyl acetate hexane=10:1) to give the intended vitamin D compound (4.9 mg, yield 68%) shown in the rightmost column in Table 7.

Physical property data for the vitamin D compound corresponding compound A $^1$H NMR: 0.54 (s, 3H), 0.84 (d, 3H, J=6.4Hz), 1.22 (s, 6H), 2.29-2.35 (m, 1H), 2.57-2.63 (m, 1H), 2.78-2.85 (m, 1H), 4.20-4.28 (m, 1H), 4.39-4.46 (m, 1H), 5.00 (s, 1H), 5.32 (s, 1H), 6.01 (d, 1H, J=11.4Hz), 6.37 (d, 1H, J=11.4Hz).

UV: λmax 266 nm, λmin 229 nm.

The vitamin D compounds corresponding to compounds B to F can also be prepared in the same manner as described above. Alternatively, the protective groups on compounds B to F may be removed by any other known method, e.g., by using AG 50W-X4 (Steroids, 67, 2002, 247).

TABLE 7

| Compound No. | Wittig reagent | Ketone | Actual and percent yields of the compound obtained | Intended vitamin D compound |
|---|---|---|---|---|
| Compound A | Baggiolini E. et. al., J. Org. Chem., 51, 1986, 3098 | Sicinski R. et. al., J. Med. Chem., 41, 23, 1998, 4662 | 12.5 mg 87% | Binderup L., et al., Biochemical Pharmacology, 42, 8, 1991, 1569 |
| Compound B | Sicinski R. et. al., J. Med. Chem., 41, 23, 1998, 4662 | Sicinski R. et. al., J. Med. Chem., 41, 23, 1998, 4662 | 13.6 mg 95% | Sicinski R. et. al., J. Med. Chem., 41, 23, 1998, 4662 |

TABLE 7-continued

| Compound No. | Wittig reagent | Ketone | Actual and percent yields of the compound obtained | Intended vitamin D compound |
|---|---|---|---|---|
| Compound C | Baggiolini E. et. al., J. Org. Chem., 51, 1986, 3098 | Baggiolini G. et. al., J. Am. Chem. Soc., 104, 10, 1982, 2945 | 6.8 mg 47% | |
| Compound D | Kato P. et. al., Tetrahedron Lett., 32, 52, 1991, 7663 | Baggiolini G. et. al., J. Am. Chem. Soc., 104, 10, 1982, 2945 | 8.7 mg 62% | Perlman K. et al., Tetrahedron Lett., 32, 52, 1991, 7663 |

TABLE 8
| Compound No. | Wittig reagent | Ketone | Actual and percent yields of the compound obtained | Intended vitamin D compound |
|---|---|---|---|---|
| Compound E | Baggiolini E. et al., J. Org. Chem., 51, 1986, 3098 | Hatakeyama S. et al., Bioorg. Med. Chem., 9, 2001, 403 | 13.3 mg 92% | Kubodera N. et al., Chem. Pharm. Bull., 41, 9, 1993, 1659 |
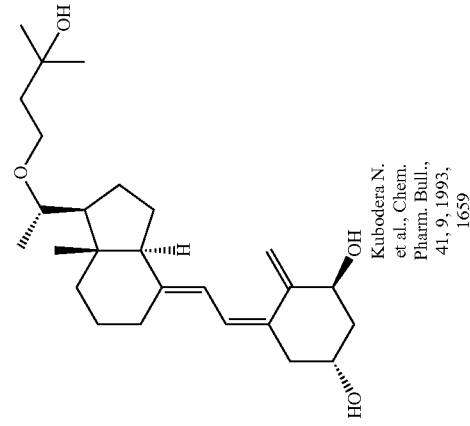

TABLE 8-continued
| Compound No. | Wittig reagent | Ketone | Actual and percent yields of the compound obtained | Intended vitamin D compound |
|---|---|---|---|---|
| Compound F | 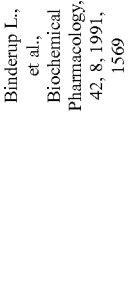 Baggiolini E. et. al., J. Org. Chem., 51, 1986, 3098 | 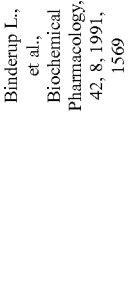 Posner G. et. al., J. Org. Chem., 62, 1997, 3299 | 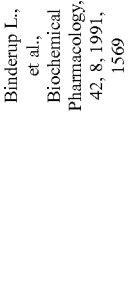 13.9 mg 91% | 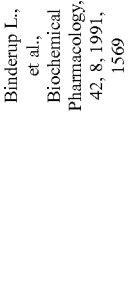 Binderup L., et al., Biochemical Pharmacology, 42, 8, 1991, 1569 |

Example 2

A 0.22M solution of the Wittig reagent shown in Table 9 in benzene (100 μL, 22 μmol) was added into a reaction vessel at room temperature, and the benzene was distilled off at room temperature and the residue was dried under reduced pressure at room temperature for 3 hours. The resulting residue was dissolved in 200 μL of tetrahydrofuran in a nitrogen atmosphere at room temperature, and 22 μmol of the aldehyde shown in Table 9 was added at room temperature, and the solution was stirred at room temperature and then cooled to −20° C. To the mixture was added 2 μL of a 1M solution of lithium bistrimethylsilylamide in tetrahydrofuran at room temperature every second eleven times (22 μL, 22 μmol in total) with stirring. Then, the reaction mixture was stirred at 50° C. for 16 hours. After the reaction was complete, the solvent was distilled off. The residue was purified by preparative TLC (Merk, silica gel 60, eluted with ethyl acetate:hexane=1:20) to give compound G.

$^1$H NMR for compound G: 4.10 (m, 1 H), 4.37-4.41 (m, 1H), 4.87 (s, 1H), 5.19 (s, 1H), 5.59 (dd, 1H, J=6.5, 16.5Hz), 5.88 (d, 1H, J=10.8Hz), 6.34 (dd, 1H, J=10.8, 16.5Hz).

Compound G is an intermediate of its corresponding vitamin D compound, and the intended vitamin D compound can be obtained by removing the protective groups by any known method, e.g. by using tetraammonium fluoride (Bioorg. Med. Chem. 9 (2001) 403) or by using AG 50W-X4 (Steroids, 67, 2002, 247), etc.

reagent in benzene (100 μL, 22 μmol) were added into a reaction vessel at room temperature, and the benzene was distilled off from the resulting mixture at room temperature and the residue was dried under reduced pressure for 3 hours at room temperature. The resulting residue was dissolved in 200 μL of tetrahydrofuran in a nitrogen atmosphere at room temperature, and 2 μL of a 1 M solution of lithium bistrimethylsilylamide in tetrahydrofuran at room temperature was added to the mixture every second eleven times (22 μL, 22 μmol in total) with stirring at room temperature, and the solution was mixed with stirring. Then, the reaction mixture was stirred at 50° C. for 16 hours. After the reaction was complete, the solvent was distilled off. The residue was purified by preparative TLC (Merk, silica gel 60, eluted with ethyl acetate:hexane=1:20) to give compound H.

$^1$H NMR for compound H: 0.53 (s, 3H), 1.20 (s, 6H), 4.15-4.22 (m, 1 H), 4.37-4.42 (m, 1H), 4.87 (s, 1H), 5.17 (s, 1H), 6.01 (d, 1H, J=11.4Hz), 6.23 (d, 1H, J=11.4Hz).

The ketone used as a starting material for the synthesis can be synthesized by the method described in the document shown in the table.

Compound H is an intermediate of its corresponding vitamin D compound, and the intended vitamin D compound can be obtained by removing the protective groups by any known method, e.g. by using tetraammonium fluoride (Bioorg. Med. Chem. 9 (2001) 403) or by using AG 50W-X4 (Steroids, 67, 2002, 247), etc.

TABLE 9

| Wittig reagent | Aldehyde | Actual and percent yields of compound G |
|---|---|---|
| 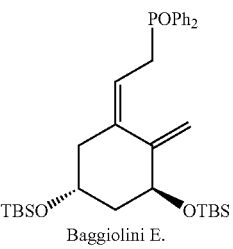<br>Baggiolini E. et. al., J. Org. Chem., 51, 1986, 3098 | 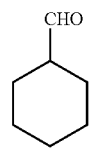 | 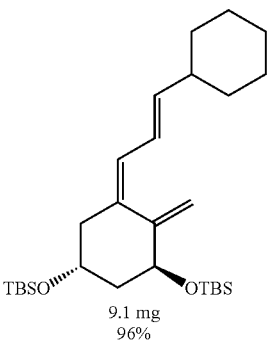<br>9.1 mg<br>96% |

Example 3

A 0.3M solution of the ketone shown in Table 10 in benzene (66.6 μL, 20 μmol) and a 0.22M solution of the Wittig TABLE 10
| Wittig reagent | Ketone | Actual and percent yields of the compound obtained | Intended vitamin D compound |
|---|---|---|---|
| 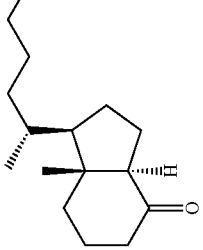 Baggiolini E. et. al., J. Org. Chem., 51, 1986, 3098 | 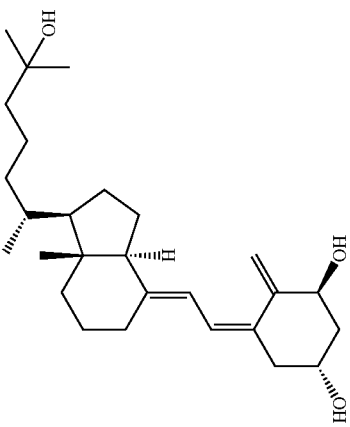 G. Baggiolini et. al., J. Am. Chem. Soc., 104 10, 1982, 2945 | 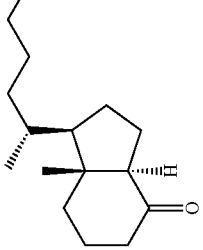 6.3 mg 43% | 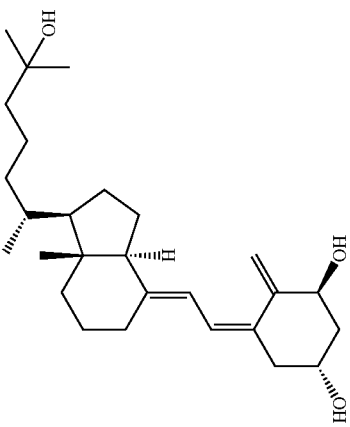 |

Example 4

A 0.22M solution of the Wittig reagent shown in Table 11 in benzene (100 μL, 22 μmol) was added into a reaction vessel at room temperature, and the benzene was distilled off at room temperature and the residue was dried under reduced pressure at room temperature for 3 hours. The resulting residue was dissolved in 200 μL of tetrahydrofuran in a nitrogen atmosphere at room temperature, and 22 μmol of the aldehyde shown in Table 11 was added at room temperature, and 2 μL of a 1M solution of lithium bistrimethylsilylamide in tetrahydrofuran at room temperature was added to the mixture every second eleven times (22 μL, 22 μmol in total) with stirring at room temperature. Then, the reaction mixture was stirred at 50° C. for 16 hours. After the reaction was complete, the solvent was distilled off. The residue was purified by preparative TLC (Merk, silica gel 60, eluted with ethyl acetate:hexane=1:20) to give compound G.

$^1$H NMR for compound G: 4.10 (m, 1H), 4.37-4.41 (m, 1H), 4.87 (s, 1H), 5.19 (s, 1H), 5.59 (dd, 1H, J=6.5, 16.5Hz), 5.88 (d, 1H, J=10.8Hz), 6.34 (d, 1H, J=10.8, 16.5Hz).

Compound G is an intermediate of its corresponding vitamin D compound, and the intended vitamin D compound can be obtained by removing the protective groups by any known method, e.g. by using tetraammonium fluoride (Bioorg. Med. Chem. 9 (2001) 403) or by using AG 50W-X4 (Steroids, 67, 2002, 247), etc.

Example 5

A 0.3M solution of the ketone shown in Table 12 in benzene (66.6 μL, 20 μmol) and a 0.22M solution of the Wittig reagent in benzene (100 μL, 22 μmol) were added into a reaction vessel at room temperature, and the benzene was distilled off from the resulting mixture at room temperature and the residue was dried under reduced pressure for 3 hours at room temperature. The resulting residue was dissolved in 200 μL of tetrahydrofuran in a nitrogen atmosphere at room temperature, and the solution was cooled to −20° C. To the resulting mixture was added 13.9 μL of a 1.58 M solution of n-butyl lithium in hexane at room temperature over 5 minutes at −20° C. with stirring. Then, the reaction mixture was stirred at −20° C. for 2 hours and then slowly warmed to room temperature and stirred at room temperature for further 2 hours. After the reaction was complete, the solvent was distilled off. The residue was purified by preparative TLC (Merk, silica gel 60, eluted with ethyl acetate:hexane=1:20) to give compound H.

$^1$H NMR for compound H: 0.53 (s, 3 H), 1.20 (s, 6H), 4.15-4.22 (m, 1H), 4.37-4.42 (m, 1H), 4.87 (s, 1H), 5.17 (s, 1H), 6.01 (d, 1H, J=11.4Hz), 6.23 (d, 1H, J=11.4Hz).

Compound H is an intermediate of its corresponding vitamin D compound, and the intended vitamin D compound can be obtained by removing the protective groups by any known method, e.g. by using tetraammonium fluoride (Bioorg. Med. Chem. 9 (2001) 403) or by using AG 50W-X4 (Steroids, 67, 2002, 247), etc.

TABLE 11

| Wittig reagent | Aldehyde | Actual and percent yields of Compound G |
|---|---|---|
| 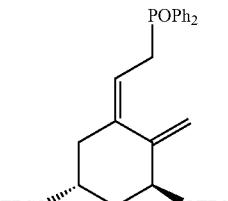 Baggiolini E. et. al., J. Org. Chem., 51, 1986, 3098 | 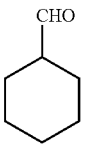 | 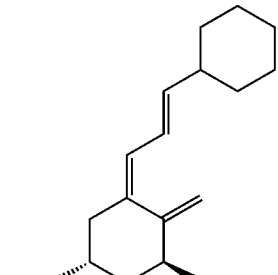 8.1 mg 85% |

TABLE 12

| Wittig reagent | Ketone of Compound H | Actual and percent yields |
|---|---|---|
| 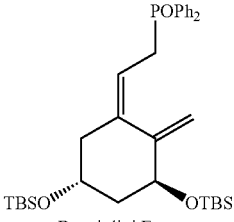<br>Baggiolini E. et. al., J. Org. Chem., 51, 1986, 3098 | 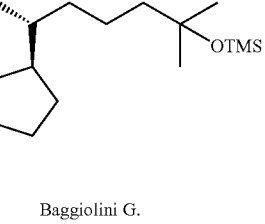<br>Baggiolini G. et. al., J. Am. Chem. Soc., 104, 10, 1982, 2945 | 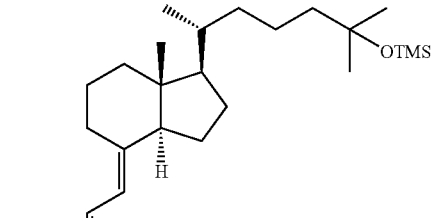<br>5.8 mg<br>41% |

| Wittig reagent | | Intended vitamin D compound |
|---|---|---|
| 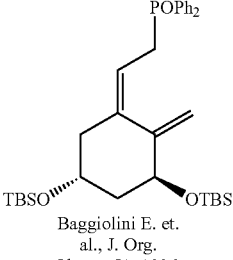<br>Baggiolini E. et. al., J. Org. Chem., 51, 1986, 3098 | | 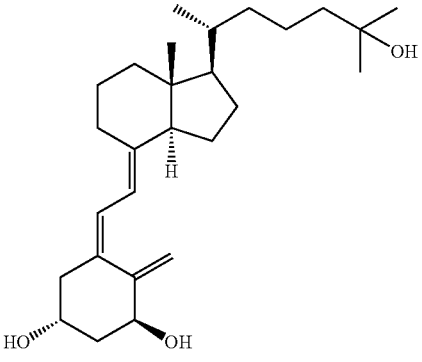 [SMILES: C=C1/C(=C\C=C2/CCC[C@]3(C)[C@@H]([C@H](C)CCCC(C)(C)O)CC[C@@H]23)C[C@@H](O)C[C@@H]1O] |

INDUSTRIAL APPLICABILITY

According to the processes of the present application, vitamin D compounds and their intermediates can be formed by simpler procedures than used in conventional processes.

The invention claimed is:
1. A process for preparing a vitamin D compound of formula (I) and an intermediate thereof:

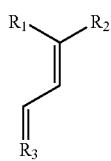 (I)

wherein $R_1$ and $R_2$ are the same as $R_5$ and $R_6$ defined below, respectively, and $R_3$ is the same as $R_8$ defined below, comprising the steps of:
(a) mixing a ketone of formula (II):

$R_5COR_6$  (II)

wherein $R_5$ and $R_6$ are joined to form a bicyclo[4.3.0]nonanyl having one or more substituents or a bicyclo[4.3.0]nonenyl having one or more substituents, with an allylphosphine oxide derivative of formula (IV):

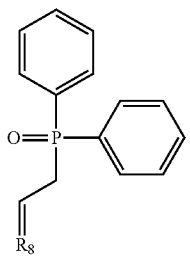 (IV)

wherein $R_8$ represents a cyclohexanyl optionally substituted and optionally containing one or more double bonds, in a solvent having no influence on the reaction between the ketone and the allylphosphine oxide derivative;
(b) evaporating the mixture to dryness to remove water, and dissolving the residue in another solvent;
(c) cooling the resulting solution to a temperature of about −20° C. to room temperature; and
(d) adding a base dropwise to the solution at a temperature of about −20° C. to room temperature;
wherein the cyclohexanyl represented by $R_8$ is optionally substituted with one or more substituents selected from the group consisting of hydroxy, =$CH_2$, and a C1-C15 straight or branched hydrocarbon optionally containing an intervening oxygen, where the straight or branched hydrocarbon may be substituted with one or more hydroxyl groups; and wherein the substituents on $R_5$, $R_6$, and $R_8$ may be protected by a protective group.

2. The process of claim 1, wherein the compound of the formula (I) has vitamin D activity or antagonist activity against vitamin D.

3. The process of claim 1, wherein $R_5$, $R_6$, and $R_8$ are such that the vitamin D compound is of formula (V):

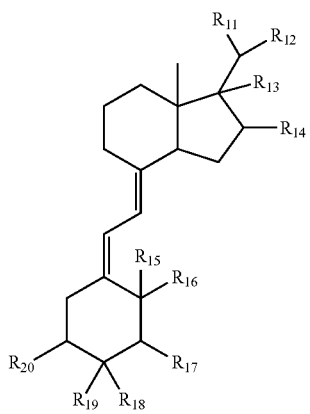

(V)

wherein $R_{11}$ and $R_{12}$ independently represent a hydrogen atom, or a C1-C30 straight or branched hydrocarbon optionally containing one or more double or triple bonds and optionally containing an intervening oxygen, nitrogen, or sulfur atom and optionally substituted by one or more $R_c$s, with the proviso that $R_{11}$ and $R_{12}$ do not simultaneously represent a hydrogen atom;

$R_{13}$ and $R_{14}$ simultaneously represent a hydrogen atom, or $R_{13}$ and $R_{14}$ are joined to form a single bond;

$R_{15}$ and $R_{16}$ simultaneously represent a hydrogen atom, or $R_{15}$ and $R_{16}$ are joined to form =$CH_2$;

$R_{17}$ represents hydroxy;

$R_{18}$ and $R_{19}$ independently represent a hydrogen atom or a C1-C6 straight or branched hydrocarbon optionally containing an intervening oxygen and optionally substituted with one or more hydroxyl groups, or $R_{18}$ and $R_{19}$ are joined to form =$CH_2$, $R_{20}$ represents hydroxy;

wherein $R_{11}$, $R_{12}$, $R_{17}$, $R_{18}$, $R_{19}$, $R_{20}$ and the substituents thereon may be protected by a protective group;

or a salt thereof.

4. The process of claim 3, wherein the compound of formula (V) has vitamin D activity or antagonist activity against vitamin D.

5. The process of claim 1, wherein the vitamin D compound is a compound having a structure represented by formula (VI) or (VII):

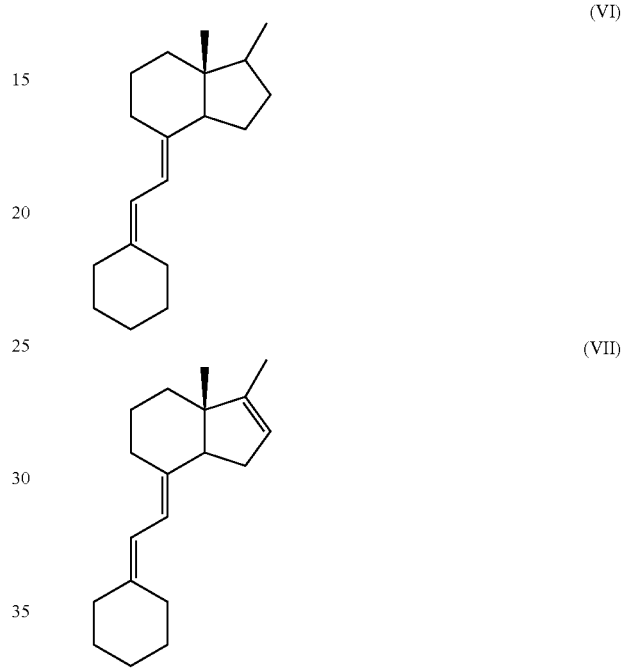

or a salt thereof, as its partial structure.

6. The process of claim 5, wherein the vitamin D compound has vitamin D activity or antagonist activity against vitamin D.

* * * * *